United States Patent
Nakagawa

(10) Patent No.: US 8,420,343 B2
(45) Date of Patent: Apr. 16, 2013

(54) ACQUISITION METHOD FOR BIOLOGICAL RHYTHM INFORMATION

(75) Inventor: Kazuhiro Nakagawa, Tokyo (JP)

(73) Assignee: Sony Corporation, Tokyo (JP)

( * ) Notice: Subject to any disclaimer, the term of this patent is extended or adjusted under 35 U.S.C. 154(b) by 379 days.

(21) Appl. No.: 12/667,180

(22) PCT Filed: Jul. 4, 2008

(86) PCT No.: PCT/JP2008/062195
§ 371 (c)(1),
(2), (4) Date: Feb. 26, 2010

(87) PCT Pub. No.: WO2009/008374
PCT Pub. Date: Jan. 15, 2009

(65) Prior Publication Data
US 2010/0184109 A1   Jul. 22, 2010

(30) Foreign Application Priority Data

Jul. 6, 2007 (JP) ................................. 2007-177952
Jul. 2, 2008 (JP) ................................. 2008-173267

(51) Int. Cl.
*C12Q 1/40* (2006.01)

(52) U.S. Cl.
USPC ........................................................ 435/22

(58) Field of Classification Search ............. 435/22
See application file for complete search history.

(56) References Cited

U.S. PATENT DOCUMENTS

2006/0078883 A1* 4/2006 Ueda et al. ................. 435/6
2007/0105180 A1* 5/2007 Shaw et al. ................ 435/22

FOREIGN PATENT DOCUMENTS

| JP | 6-189914 | 7/1994 |
|----|----------|--------|
| JP | 2002-168860 | 6/2002 |
| JP | 2005-80603 | 3/2005 |
| JP | 2006-345869 | 12/2006 |
| JP | 2006-345870 | 12/2006 |
| WO | WO 2004/012128 A1 | 2/2004 |

OTHER PUBLICATIONS

Rietveld W. J. et al. Circadian Rhythmicity in Human Buccal Epithelial Cells in Relation to Saliva Enzyme Activity. Chronobiologia 10(2)152, 1983.*
Bellavia S. L. et al. Alpha Amylase Circadian Rhythm of Young Rat Parotid Gland. Archives of Oral Biology 37(5)429-433, 1992.*
Sanz E. et al. Ontogeny of Alpha Amylase Circadian Rhythms in Rat Parotid Gland. Comparative Biochemistry Physiology 85A(3)571-574, 1986.*
Ciuk M. et al. Rhythmic Oscillations of Alpha Amylase Protein and its Enzymatic Activity Levels in DM. European J Entomology 106:519-528, 2009.*
G.A. Bjarnason et al., "Circadian Expression of Clock Genes in Human Oral Mucosa and Skin", American Journal of Pathology, vol. 158, No. 5, pp. 1793-1801, XP008134354 (2001).
S.N. Safarova, "Circadian Rhythm of the Enzyme Activity of Small Intestine Mucosa in Horsefield's Terrapins", Uzbekskii Biologicheskii Zhurnal, Uzbekiston SSR Fanlar Akademisi Nasrieti, No. 2, pp. 28-30, XP008134315 (1989).
M.A. Barrat et al., "Circadian variations of dehydropyrimidine dehydrogenase (DPD) activity in oral mucosa of healthy volunteers" Pathologie et Biologie, L'Expansion Scientifique Francaise, vol. 51, No. 4, pp. 191-193, XP008134355 (2003).
W.J. Rietveld et al., Circadian Rhythmicity in Human Buccal Epithelial Cells in Relation to Saliva Enzyme Activity, Chronobiologia, vol. 10, No. 2, p. 152, XP008134351 (1983).
C. Cajochen et al., "Evening exposure to blue light stimulates the expression of the clock gene PER2 in humans", European Journal of Neuroscience, vol. 23, pp. 1082-1086, XP0081345357 (2006).
Supplementary European Search Report issued Mar. 22, 2011 in The Hague in EP 08 77 7910.
J. Oral Bioschi, "Journal of Oral Biosciences" vol. 47, pp. 78, Suppl. Jan. 2005.
Laurent Seugnet et al., "Identification of a Biomarker for Sleep Drive in Flies and Humans". vol. 103, No. 52. pp. 19913-19918, Dec. 26, 2006.

* cited by examiner

*Primary Examiner* — Ralph Gitomer
(74) *Attorney, Agent, or Firm* — Finnegan Henderson Farabow Garrett & Dunner LLP

(57) ABSTRACT

A simple low-invasive method for acquiring information about a biological rhythm of a bion is provided. In the method, the information on a biological rhythm of the bion is acquired based on variation with time of the activity of a biologically active agent, particularly alpha-amylase, extracted from oral mucosa epithelial cells of the bion. According to the method, an activity variation curve showing the variation of the activity of the biologically active agent with time may be utilized as a molecular timetable for estimation of the biological rhythm, whereby a deviation (lag) of the biological rhythm of the bion can be detected.

12 Claims, 4 Drawing Sheets

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
tggcaactgc acaggcatta                                            20

<210> SEQ ID NO 2
<211> LENGTH: 19
<212> TYPE: DNA
<213> ORGANISM: Artificial
```

```
<220> FEATURE:
<223> OTHER INFORMATION: Synthetic oligonucleotide

<400> SEQUENCE: 2
tgctttgcgg atttgcatt                                              19
```

ACQUISITION METHOD FOR BIOLOGICAL RHYTHM INFORMATION

This application is a national stage entry of PCT Application No. PCT/JP2008/062195, filed Jul. 4, 2008, which claims priority to Japanese Patent Application No. 2008-173267, filed Jul. 2, 2008, and Japanese Patent Application No. 2007-177952, filed Jul. 6, 2007.

TECHNICAL FIELD

The present invention relates to a method for acquiring information about a biological rhythm of a bion. More particularly, the invention relates to a method for acquiring information particularly about a circadian rhythm, based on variations with time of activity value of a biologically active agent extracted from oral mucosa epithelial cells of a bion.

BACKGROUND ART

It is known that various biophenomena in a bion each show a "periodic rhythm" which vibrates in a self-supporting manner. This periodic rhythm is called "biological rhythm." Especially, a "circadian rhythm" having a period (cycle time) of about one day governs widely the biophenomena such as the sleep-wake rhythm and diurnal variations in body temperature, blood pressure and quantities of hormones secreted. In addition, the circadian rhythm is known to relate also to mental and physical activities, capacity for locomotion, drug sensitivity, and so on.

The biological rhythm is controlled by a gene group called "clock gene." The clock gene (which may hereinafter be referred to also as "clock molecule") functions as a "biological clock" by autonomously periodically varying (vibrating) the expression, activity, localized presence or the like thereof. Specifically, by controlling other various kinds of gene groups, the clock gene governs the above-mentioned various biophenomena. It is considered that the biological clocks based on the clock molecules are present on a variety of levels of each of cells, tissues and organs in the living body of a bion, and the biological clocks are synchronized with each other to create the biological rhythm of the bion as a whole.

It has been clarified that gene polymorphism and gene mutation of the clock molecule would be critical causes of cancer, diabetes, vascular diseases, altered-nerve diseases and the like. In recent years, furthermore, it has been pointed out that a gene polymorphism or mutation of the clock molecule relates also to the crisis of mental disorders such as bipolar disorder and depression. In connection with this, a therapeutic method has been tried in which the biological clock having been brought out of order due to a gene polymorphism or mutation is reset by irradiation with light.

On the other hand, the sleep-wake cycle, for example, is not only autonomously controlled by the biological clock but also is under restrictions by social life. Thus, a change in the bedtime or the rising time in daily life may cause a rhythm deviation (phase deviation) between the "going-to-bed and rising cycle in real life" and the "sleep-wake cycle based on the biological clock." Such a deviation (lag) of rhythm is considered to induce the so-called "jet lag" or somnipathy and, further, to cause the above-mentioned mental disorders.

A deviation (lag) generated between the so-called "external time" and the so-called "internal time," such as that between the "going-to-bed and rising cycle in real life" and the "sleep-wake cycle based on the biological clock," is deemed as an "internal desynchronization" of biological rhythm. The "internal desynchronization" can be said to be a state in which the biological clocks of organs in a living body are desynchronized. The internal desynchronization is considered to arise from the fact that the biological clocks of the organs differ from each other in readiness to get synchronous, so to speak the speed of synchronization, with the external time. It is known that when an internal desynchronization is generated, a biphasic rhythm comes to be observed in the diurnal variations of body temperature, blood pressure, etc. Attempts to maximize the effect of pharmacotherapy by utilizing the biological rhythm have begun. Due to the amount of expression of a molecule serving as a target of a drug (drug target molecule) and the circadian rhythm of an enzyme which metabolizes the drug (drug-metabolizing enzyme), the therapeutic effect of the drug is also considered to show a diurnal variation. Taking this into account, there has been proposed a way of thinking called "chronotherapy" in which maximization of a therapeutic effect is contrived by determining an optimal medication time for each drug.

Besides, in a more familiar aspect, the acting time for bringing out personal ability to the full in learning or trailing and the eating time for a person to get fat with difficulty (or with ease) have come to be investigated utilizing the circadian rhythms of mental and physical activities and capacity for locomotion.

From the foregoing, it is considered that to accurately know the biological rhythm based on a biological clock is very useful for prevention of various diseases, for improvement of poor physical condition such as jet lag, for realization of chronotherapy, for exhibition of personal ability, for a diet, and so on.

PCT Patent Publication No. WO 2004/012128 discloses at least a method for estimating a biological time on the basis of gene expression product amount measurement data on a standard specimen taken as a sample from a bion. In the biological clock estimation method, a molecular timetable for estimation of a biological clock is formed based on the expression amount of a gene expression product (specifically, mRNA). Incidentally, PCT Patent Publication No. WO 2004/012128 does not describe a specific tissue (or cell) to be taken as a sample or a specific gene to be measured.

Japanese Patent Laid-open No. Hei 6-189914 describes a biological rhythm curve measuring apparatus for measuring a biological rhythm curve from measured values of deep body temperature of a human being. In the biological rhythm curve measuring apparatus, a contrivance is made such that a true biological rhythm curve can be measured through removing influences of disturbances (external influences). Incidentally, Japanese Patent Laid-open No. Hei 6-189914 shows rectal temperature or tympanic temperature as a specific example of the deep body temperature, and describes that the rectal temperature is particularly preferable.

In addition, as inventions relating to the present invention, Japanese Patent Laid-open Nos. 2002-168860, 2006-345869, and 2006-345870 may be mentioned which each disclose a method of determining stress by using as an indicator the activity of alpha-amylase in the saliva of a subject. In the stress determination method, the activity of alpha-amylase in the "saliva" is measured, whereby the degree of stress in the subject can be determined simply and easily.

The biological clock estimation method disclosed in PCT Patent Publication No. WO 2004/012128 is a method based on the expression amount of mRNA of a standard specimen taken as a sample from a bion. While PCT Patent Publication No. WO 2004/012128 does not describe a specific tissue (or cell) to be taken as a sample or a specific gene to be measured, a method of examining the expression of a clock gene in leukocyte has hitherto been adopted widely as a simple method. In this method, however, taking a sample of blood is indispensable, which is attended by a physical pain in the subject.

Furthermore, it is necessary for the measuring person to conduct an operation of separating the leukocyte from the blood taken as a sample, an operation of extracting mRNA from the leukocyte, analysis of the expression of the clock gene mRNA and the like, which has been the reason why it take much time and labor to carry out the method. In fact, in order to extract mRNA from an organism specimen and determine the mRNA, in general, an intricate operation is needed for preventing the mRNA from being decomposed. Especially, if decomposition of mRNA occurs in dealing with a very small amount of organism specimen, it would be impossible to obtain stable measurement results.

The biological rhythm curve measuring apparatus disclosed in Japanese Patent Laid-open No. Hei 6-189914 is an apparatus for measuring particularly the rectal temperature. Measurement of body temperature in the rectum, however, imposes a mental or physical pain on the subject and, therefore, the measuring person also gets a feeling of burden.

Accordingly, it is an object of the present invention to provide a simple and low-invasive method for acquiring information about a biological rhythm of a bion.

DISCLOSURE OF INVENTION

In order to attain the above object, according to the present invention, there is provided a method of acquiring information about a biological rhythm of a bion on the basis of variation with time of the activity of a biologically active agent, specifically, alpha-amylase, extracted from oral mucosa epithelial cells of the bion.

In this method, an activity variation curve showing the variation with time of the activity of the biologically active agent is utilized as a molecular timetable for estimation of the biological rhythm.

In this method, a deviation (lag) of the biological rhythm can be detected based on the number of local maxima of the activity which the activity variation curve exhibits in one day by use of the molecular timetable.

Besides, a phase deviation of the biological rhythm of the bion can be detected by carrying out a plurality of times the operation of forming a molecular timetable for the bion, and collating the molecular timetables thus formed.

Furthermore, a phase deviation of the biological rhythm of the bion can also be detected by collating the activity of the biologically active agent at a predetermined time with the molecular timetable.

According to the present invention, there is provided a simple low-invasive method for acquiring information about a biological rhythm of a bion.

BEST MODE FOR CARRYING OUT THE INVENTION

1. Biologically Active Agent

Figure 1:
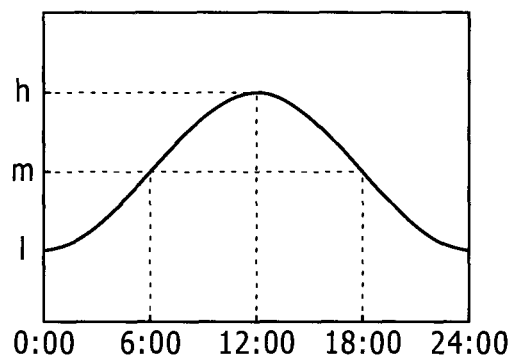
FIG. 1 is a diagram showing an example of variation of alpha-amylase activity with time.

In order to establish a method for acquiring information about a biological rhythm of a bion in a simple and low-invasive manner, the present inventor first paid attention to oral mucosa epithelial cells as a bio-tissue which can be taken as sample in an extremely low invasive manner. Then, the inventor identified alpha-amylase as a molecule showing a diurnal variation of expression amount in the oral mucosa epithelial cells, and found out that the activity of the alpha-amylase exhibits a biological rhythm. Based on the finding, the present invention has been completed.

Specifically, according to the present invention, there is provided a method of acquiring information about a biological rhythm of a bion, based on variation with time of the activity of alpha-amylase extracted from oral mucosa epithelial cells of the bion. Incidentally, the bion under consideration in the present invention is not particularly limited, and widely includes experimental animals such as mice, rats, monkeys, etc., in addition to the human being.

Alpha-amylase is known to be a digestive enzyme contained in pancreatic juice and in saliva. In addition, it has been reported that in an experiment using rodents, a circadian rhythm was observed in the quantity of alpha-amylase in a salivary gland (Bellavia SL, et. al. Circadian rhythm of alpha-amylase in rat parotid gland. Acta. Odontol. Latinoam. 1990; 5(1):13-23). However, expression of alpha-amylase occurring in the cells of oral mucosa epithelium has not hitherto been known. Besides, no investigation has been conducted on a biological rhythm pertaining to alpha-amylase in oral mucosa epithelial cells.

2. Acquisition of Biologically Active Agent

Oral mucosa epithelial cells are one of bio-tissues which can be sampled with minimum invasiveness, and are used, for example, for determination of genotype by use of genome obtained from the oral mucosa epithelial cells.

In the present invention, the oral mucosa epithelial cells can be sampled, for example, by a method wherein a sample of the cells is scraped off from the surface of the oral mucosa by use of a brush, a spatula or the like. The sampling site is preferably the mucosa on the back side of a cheek; for suppressing dispersion of the measurements, it is desirable to take the sample from the mucosae on both the left and right sides.

The oral mucosa epithelial cells sampled by the brush or the like can be recovered into a buffer by a method wherein the brush or the like is washed in a buffer, such as a phosphate buffer (PBS), contained in a sample tube. In this case, for preventing the cells from being dissolved, an isotonic solution is used as the buffer.

The cell-containing suspension obtained in this manner is subjected to centrifugation or filtration so as to separate the oral mucosa epithelial cells. The centrifugation or filtration may be carried out by the usual method. In order to eliminate the saliva having mixed into the suspension at the time of sampling the oral mucosa epithelial cells, however, the operation of centrifugation or filtration is desirably carried out a plurality of times. A large quantity of alpha-amylase secreted from the saliva gland is present in the saliva, and, when this alpha-amylase is mixed into the cells separated as above, it becomes impossible to accurately measure the activity of only the alpha-amylase present in the oral mucosa epithelial cells.

The cells separated as above are dissolved for preparation of a protein extract. The dissolution of the cells may be carried out by use of, for example, a buffer with a commercialized protein extraction reagent or surface active agent added thereto. Besides, the dissolution may be carried out by a method in which the buffer with the cells suspended therein is subjected to physical cell crushing such as an ultrasonic treatment. The cell solution is subjected to centrifugation or filtration to remove insoluble matter therefrom, whereby a protein extract is prepared.

The measurement of the alpha-amylase activity in the protein extract prepared as above can be carried out by adopting a known method, in which a commercialized measuring device or measuring kit can be used. Incidentally, a specific method for measurement will be described in Examples later.

Thus, in the method according to the present invention, use is made of the oral mucosa epithelial cells which can be sampled easily. Therefore, the mental and/or physical burden on the subject can be extremely lightened, as compared with the methods according to the related art.

In addition, since the protein which is more stable than mRNA is adopted as an object of measurement, an intricate operation is unnecessary and stable measurement results can be obtained through a simple operation, unlike the methods according to the related art. Furthermore, while analysis of expression of mRNA in general takes about two hours, the measurement of the alpha-amylase activity can be completed within several minutes by use of a commercialized measuring device which will be described later. Thus, the measurement results can be obtained in a short time.

3. Molecular Timetable

FIG. 1 is a diagram showing variation of alpha-amylase activity with time. The diagram shows an example of an activity variation curve obtained by a method in which measurement of alpha-amylase activity in oral mucosa epithelial cells by the above-mentioned method is carried out at each of predetermined times in one day and the measured values of the activity are plotted. In the diagram, time is taken on the axis of abscissas, and the activity on the axis of ordinates. In this diagram, a case where a minimum activity (l) is measured at 0:00 and a maximum activity (h) at 12:00 is shown as an example.

The activity variation curve can be obtained by inspection or observation of the plots of the activity values measured at the respective times. Besides, in order to obtain a more accurate curve, use can be made of such period (cycle time) calculation methods as an autocorrelation method (correlogram), a power spectrum method, a cosinor method, a periodogram method, etc.

As seen in the diagram, the activity of alpha-amylase undergoes a diurnal variation, showing a circadian rhythm. Therefore, information on a biological rhythm in a subject bion can be obtained based on the variation of alpha-amylase activity with time. Besides, the biological rhythm of the subject bion can be estimated by utilizing the activity variation curve of alpha-amylase as a "molecular timetable."

Specifically, it is assumed, for example, that for a subject bion known to have the activity variation curve (hereinafter used in the same meaning as the "molecular timetable") shown in FIG. 1, the activity value measured at a predetermined time is h. In this case, based on the activity variation curve (molecular timetable) shown in FIG. 1, the circadian rhythm (internal time) in the subject bion can be estimated to be at 12:00. Similarly, in the case where the activity value is l, the circadian rhythm (internal time) in the subject bion can be estimated to be at 0:00. Further, where the activity value is m, the circadian rhythm (internal time) can be estimated to be at 6:00 or 18:00.

Besides, for the same subject bion as above, it is assumed for example that the two activity values measured at an interval of three hours are p and q, respectively. If q is higher than p ($p<q$), the circadian rhythm (internal time) in the subject bion can be estimated to be in the morning (0:00 to 12:00) corresponding to a rising stage of the activity. On the contrary, if q is lower than p ($p>q$), the circadian rhythm (internal time) can be estimated to be in the afternoon (12:00 to 24:00). Furthermore, by determining the variation ratio (q/p) of p and q and collating the variation ratio with the inclinations of tangents to the activity variation curve, the internal time in the circadian rhythm can be estimated more accurately.

4. Detection of Deviation of Biological Rhythm

Now, methods of detecting a deviation (lag) of a biological rhythm in a subject bion by way of a change in the activity variation curve will be described below.

The shape of an activity variation curve can be characterized by its maximum (or minimum), the observation time of the maximum (or minimum), the inclination of the curve from the maximum to the minimum (or from the minimum to the maximum), and so on. In the present invention, the shape of the activity variation curve will be referred to as "phase." In addition, the shape of the circadian rhythm in a subject bion specified by the activity variation curve will also be referred to as "phase."

Specifically, the activity variation curve (molecular timetable) shown in FIG. 1 has a shape, or "phase," which is characterized by the minimum l, the maximum h, the observation time (external time) 0:00 of the minimum, and the observation time 12:00 of the maximum.

(4-1) Method by Detection of Diphasic Rhythm

First, a method of detecting a deviation (lag) of a biological rhythm on the basis of the number of maxima of the activity which the activity variation curve shows in one day, by use of the molecular timetable, will be described.

As has been described above, the deviation (lag or discrepancy) generated between the "external time" and the "internal time" in a biological rhythm is regarded as "internal desynchronization." It is known that when the internal desynchronization is generated, a diphasic rhythm comes to be observed in the diurnal variations of body temperature, blood pressure, and the like. Therefore, by detection of the diphasic rhythm, it is possible to detect the internal desynchronization, that is, a deviation (lag) of the biological rhythm.

The present inventors found out that a polyphasic rhythm capable of serving as an indicator of internal desynchronization can be detected also in a diurnal variation of alpha-amylase activity, like in the diurnal variations of body temperature, blood pressure, and so on, as will be described in detail in Examples.

Figure 2:
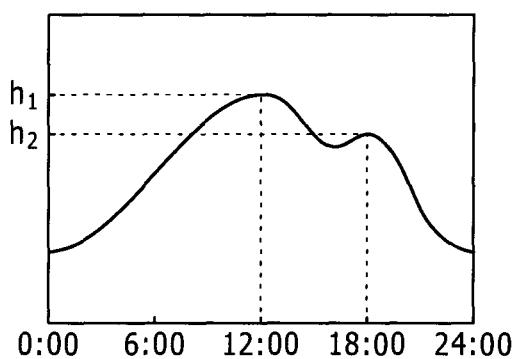
FIG. 2 is a diagram showing the phase of an activity variation curve of alpha-amylase, which exhibits a typical biphasic rhythm.

FIG. 2 is a diagram showing the phase of an activity variation curve showing a typical diphasic rhythm. This diagram represents an example of the activity variation curve in the case where internal desynchronization has been generated, in the subject bion having the activity variation curve shown in FIG. 1.

In FIG. 1, the phase of the subject bion has been characterized by the single local maximum (maximum) h and the observation time (external time) 12:00 of the local maximum (maximum). On the other hand, in the phase of the subject bion in FIG. 2, two local maxima $h_1$ and $h_2$ are appearing. Specifically, the activity variation curve shown in FIG. 2 is observed as a diphasic rhythm accompanied by two local maxima of the activity, namely, the local maximum $h_1$ at 12:00 and the local maximum $h_2$ at 18:00 in one day.

Such a plurality of maxima of the activity are considered to arise from momentary desynchronization of the biological rhythm of the subject bion as a whole, due to the fact that the biological clocks in organs differ from each other in the speed of synchronization with the external time.

Therefore, a deviation (lag) of a biological rhythm and the degree of the deviation can be detected by use of the molecular timetable, specifically on the basis of whether or not the number of local maxima of activity which the activity variation curve shows in one day is not less than two. Incidentally, the number of local maxima of activity is not limited to two, and a polyphasic rhythm accompanied by three or more local maxima of activity is observed in some cases.

Here, the observation time (external time) 12:00 of the local maximum $h_1$ at 12:00 shown in FIG. 2 coincides, in principle, with the observation time of the maximum h in the initial activity variation curve shown in FIG. 1. When internal desynchronization is generated in the biological rhythm of the subject bion, a new local maximum $h_2$ comes to be observed at a time (18:00 in FIG. 2) different from the observation time 12:00 of the maximum h. Then, the degree of internal desynchronization can be regarded as greater as the interval between the observation times (12:00 and 18:00 in the example shown) of the local maxima of activity is longer.

Furthermore, the magnitudes of the local maximum $h_1$ and the local maximum $h_2$ vary depending on the degree of the internal desynchronization generated in the subject bion. These magnitudes vary gradually as the internal desynchronization generated in the subject bion is gradually corrected and the biological rhythm of the bion as a whole is gradually synchronized. More specifically, for example, when the biological rhythm is gradually restored into the rhythm before the internal desynchronization, the local maximum $h_2$ having appeared at the observation time 18:00 disappears gradually.

In addition, where the biological rhythm is gradually synchronized with the rhythm after the internal desynchronization, on the contrary, the original local maximum $h_1$ at the observation time 12:00 gradually disappears, while the local maximum $h_2$ at 18:00 increases gradually.

Therefore, the degree of the deviation (lag) of the biological rhythm can be known, based on the magnitude of the local maximum $h_2$ in the activity variation curve shown in FIG. 2, preferably on the amplitude ratio ($h_2/h_1$) of the local maximum $h_1$ and the local maximum $h_2$. Here, the degree of the internal desynchronization is judged to be the highest in the case where the amplitude ratio ($h_2/h_1$) is approximate to 1, that is, where the local maximum $h_1$ and the local maximum $h_2$ are approximately equal.

Thus, the degree of a deviation (lag) of the biological rhythm and the condition of recovery from the deviation can be determined by use of the molecular timetable, specifically on the basis of the interval between the observation times of two or more local maxima of activity which the activity variation curve shows in one day, the magnitudes of the local maxima, and the amplitude ratio of the local maxima. Where the activity variation curve is observed as a polyphasic rhythm accompanied by three or more local maxima, the determination can be made based on the magnitudes of the local maxima and the amplitude ratio of the local maxima.

(4-2) Method by Collation of Molecular Timetables Formed a Plurality of Times

Now, a method of detecting a deviation (lag) of a biological rhythm by collation of molecular timetables formed a plurality of times for a subject bion will be described below.

Figure 3:
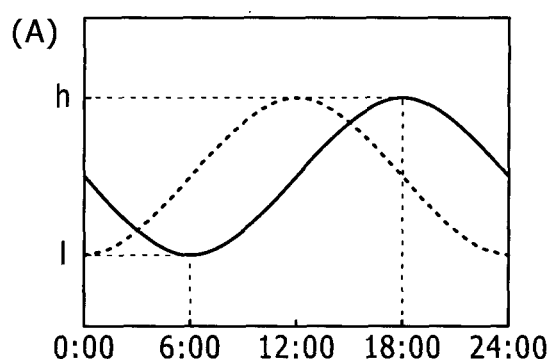
FIG. 3 show diagrams showing variations in phase of the activity variation curve of alpha-amylase.
Figure 3:
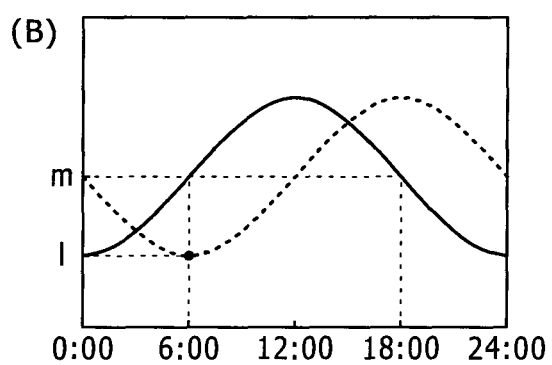

FIG. 3 shows diagrams illustrating variations in the phase of an active variation curve. In (A) of FIG. 3, the activity variation curve indicated by dotted line is the curve shown in FIG. 1 (hereinafter referred to also as "molecular timetable 1"), whereas the activity variation curve indicated by solid line represent an example of a activity variation curve obtained by the same measurement as in the case of FIG. 1 for the same subject bion but on a different measurement day (hereinafter referred to also as "molecular timetable 2"). In the diagram, time is taken on the axis of abscissas, and the activity of alpha-amylase on the axis of ordinates.

The molecular timetable 1 has a phase such that the observation time (external time) of a minimum (l) is 0:00, and the observation time of a maximum (l) is 12:00. On the other hand, the molecular timetable 2 has a changed phase such that the observation time of a minimum (l) is 6:00, and the observation time of a maximum (l) is 18:00.

This can be interpreted that a deviation (lag or discrepancy) in the activity variation curve for a subject bion is generated between the time of formation of the molecular timetable 1 and the time of formation of the molecular timetable 2. More specifically, the biological rhythm (internal time) in the subject bion at the formation time of the molecular timetable 2 has gotten six hours behind (or 18 hours ahead of) that at the formation time of the molecular timetable 1.

Thus, by forming the molecular timetable a plurality of times for the same subject bion and collating the molecular timetables with each other, the deviation (lag) of the phase of the biological rhythm in the subject bion can be detected.

(4-3) Method by Collation of Activity at Predetermined Time with Molecular Timetable Now, a method of detecting a deviation (lag) of a biological rhythm by collating the activity of a biologically active agent at a predetermined time with a molecular timetable will be described below.

The diagram in (B) of FIG. 3 shows molecular timetables by changing the molecular timetable 1 (see FIG. 1 as well) in (A) of FIG. 3 from dotted line to solid line, and the molecular timetable 2 from solid line to dotted line.

As has been described above, in the case where the activity measured at a predetermined time for a subject bion known to have the activity variation curve (molecular timetable) of FIG. 1 is m, the circadian rhythm (internal time) in the subject bion can be estimated to be 6:00 or 18:00, based on the molecular timetable 1.

Here, it is assumed that the activity obtained by measurements at 6:00 (external time) on different measurement days for the same subject bion has changed from m to l (see the round dot in (B) of FIG. 3). In this case, it can be estimated that the circadian rhythm (internal time) in the subject bion has gotten six hours behind (or 18 hours ahead of) the original, to be changed into the circadian rhythm represented by the molecular timetable 2.

Thus, by collating the activity at a predetermined time with a preliminarily formed molecular timetable, the deviation (lag) of the phase of the biological rhythm in the subject bion can also be detected more easily.

As has been described above, according to the method of the present invention, it is possible to estimate a biological rhythm intrinsic of each subject bion and to detect a deviation (lag) of the phase of the biological rhythm, by utilizing as a molecular timetable the activity variation curve showing the variation of the activity of alpha-amylase with time.

In Examples below, specific measurement data of alpha-amylase activity in oral mucosa epithelial cells will be shown. By this, it will be described that the activity of alpha-amylase exhibits a circadian rhythm and that the circadian rhythm is influenced by the rising time, resulting in generation of a deviation (lag) of the phase of the biological rhythm.

EXAMPLES

Example 1

<Identification of Alpha-amylase>

In Example 1, identification of a protein showing a circadian rhythm in oral mucosa epithelial cells was carried out.

A sample of oral mucosa epithelial cells was taken from a male adult (32 years old). The sampling was carried out eight times at 10:00, 13:00, 16:00, 19:00, 22:00, 1:00, 4:00, and 7:00, by use of a commercialized oral mucosa epithelium sampling brush (CYB-1, produced by Medical Packaging Corporation). After the sample of oral mucosa epithelial cells was taken, the brush was washed in PBS reserved in a tube, to recover the cells in the PBS. The suspension containing the cells was subjected to centrifugation (3,000 rpm, 30 sec), the oral mucosa epithelial cells thus separated were dissolved in a protein extraction buffer (RIPA Buffer, produced by PIERCE Biotechnology), and the resulting solution was also subjected to centrifugation (3,000 rpm, 30 sec), to prepare a protein extract.

Figure 4:
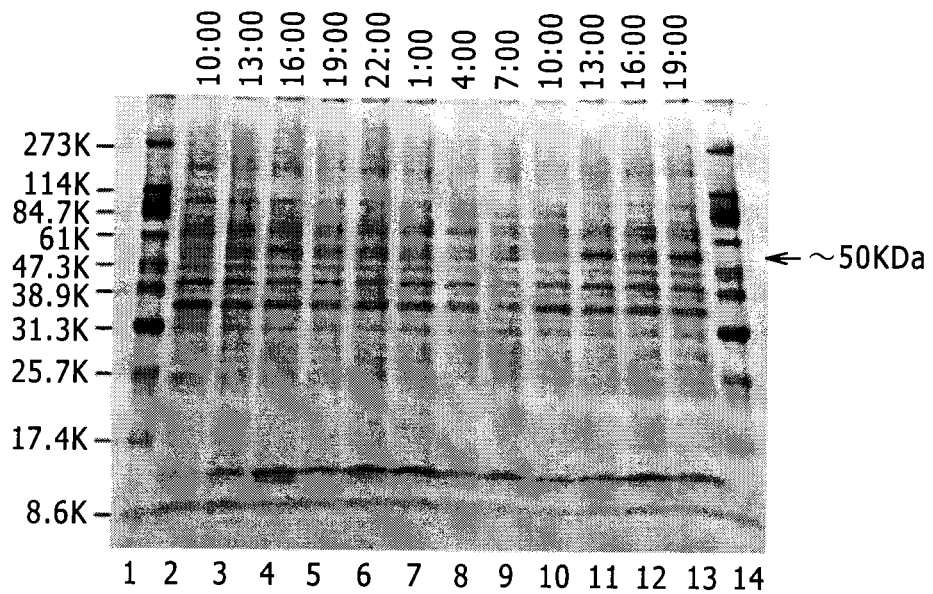
FIG. 4 is a chromatic figure of a protein extracted from oral mucosa epithelial cells.

The protein extract obtained above was subjected to polyacrylamide gel electrophoresis (SDS-PAGE) according to the usual method. FIG. 4 shows chromatic figures of the proteins obtained by subjecting the acrylamide gel after the electrophoresis to Coomassie (CBB) dyeing. In the figure, lanes 1 and 14 are molecular weight markers (molecular weight is indicated at the left of the figure). Lanes 2 to 13 are proteins extracted from the oral mucosa epithelial cells sampled at the above-mentioned times. In the figure, regarding the protein of about 50 kDa indicated by arrow (hereinafter referred to as the "object protein"), a diurnal variation of expression amount is recognized.

Figure 5:
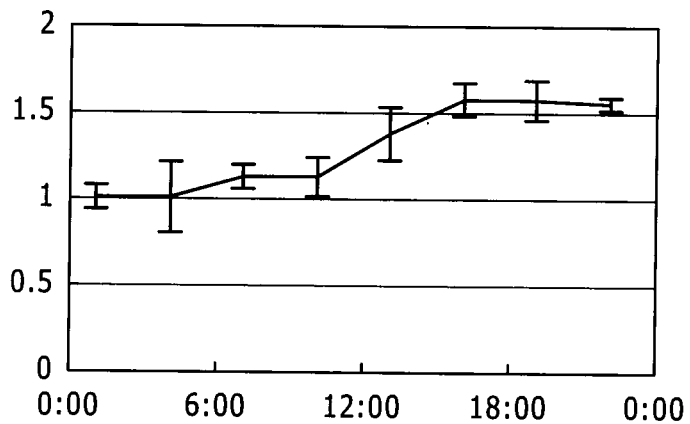
FIG. 5 is a diagram showing the expression amount of an object protein at each of specific times.

FIG. 5 is a diagram showing the expression amount of the object protein at each of the above-mentioned times. As for the expression amount, the bands of the object protein in the chromatic figures shown in FIG. 4 were quantitatively determined by densitometry, the determined values were standardized with the total quantity of proteins in each sample, and the standardized expression amounts were presented in relative values, taking the value at 1:00 as 1 (10:00, 13:00, 16:00, 19:00: n=6, 22:00, 1:00, 4:00, 7:00: n=3).

Subsequently, the object protein was subjected to protein identification by peptide mass fingerprint analysis. The band of the object protein was blanked from the acrylamide gel, the blanked gel was subjected to In-Gel digestion by trypsin, and a peptide fragment was extracted from the gel. The peptide fragment thus obtained was analyzed by a mass spectrometer (oMALDI-Qq-TOF MS/MS QSTAR Pulsar i, a TOF-MS produced by Applied Biosystems), and the analytical result was collated with NCBInr (Taxonomy human) by use of a MASCOT (produced by Matrix Science), to thereby identify the protein. Consequently, the object protein was identified as alpha-amylase.

From the results of Example 1 as above, the protein showing a circadian rhythm in the oral mucosa epithelial cells could be identified as alpha-amylase.

Example 2

<Confirmation of Expression of Alpha-amylase in Oral Mucosa Epithelial Cells>

In Example 2, an experiment for confirming the expression of alpha-amylase occurring in oral mucosa epithelial cells was carried out.

From oral mucosa epithelial cells separated by the same method as in Example 1, RNA was extracted by use of a commercialized Total RNA extraction and purification kit (produced by Agilent Technologies), and the RNA was subjected to RT-PCR according to the usual method. The sequences of primers used here are shown in "Table 1" below.

TABLE 1

| Forward Primer | tggca actgc acagg catta | Sequence No. 1 |
|---|---|---|
| Reverse Primer | tgctt tgcgg atttg catt | Sequence No. 2 |

Figure 6:
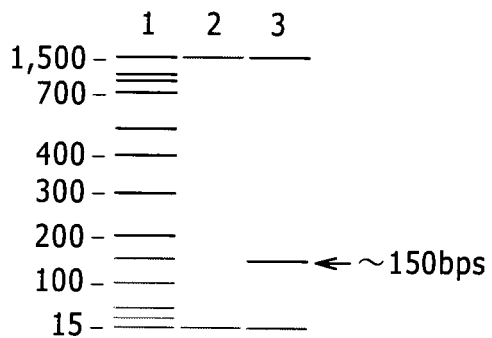
FIG. 6 is a chart showing the results of RT-PCR of alpha-amylase.

FIG. 6 is a diagram showing a migration image (chromatic figure) of a DNA fragment amplified by RT-PCR. In the diagram, lane 1 is a DNA size marker; lane 2 is a negative control; and lane 3 corresponds to the oral mucosa epithelial cells.

As shown in the diagram, amplification of a DNA fragment (indicated by arrow in the diagram) at about 150 bps is confirmed. Thus, expression of alpha-amylase mRNA in the oral mucosa epithelial cells was confirmed.

Next, in order to confirm the expression of alpha-amylase on a protein level, the following experiment was carried out.

In the same method as in Example 1, a sample of oral mucosa epithelial cells was taken, and then the brush was washed in PBS contained in a tube, to obtain a suspension containing the cells. The suspension of the cells was subjected to measurement of the activity of alpha-amylase. The measurement was conducted by use of a Salivary a-Amylase Assay Kit (produced by Salmetrics).

Figure 7:
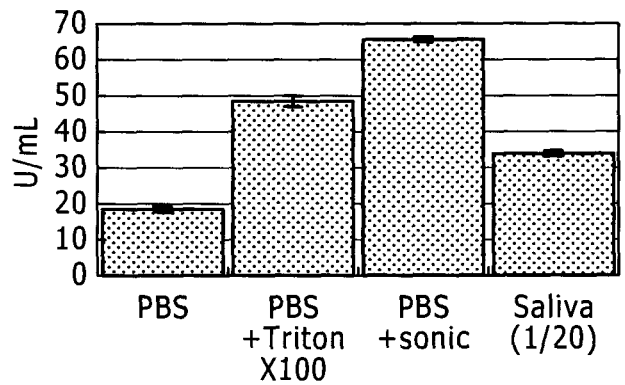
FIG. 7 is a diagram showing alpha-amylase activities of a suspension of oral mucosa epithelial cells and a solution of the cells.

FIG. 7 is a diagram showing the activity of alpha-amylase. In the diagram, "PBS" indicates the activity (about 20 U/ml) measured for the suspension of the cells. Since the suspension of the cells did not contain the oral mucosa epithelial cells in dissolved state, the activity measured for the suspension is considered to arise from the alpha-amylase contained in the saliva mixed into the suspension through adhesion to the brush at the time of taking the sample of the oral mucosa epithelial cells. In the diagram, "Saliva" indicates the activity of the alpha-amylase present in the saliva diluted with PBS by a factor of 20.

In the diagram, "PBS+TritonX100" and "PBS+Sonic" each indicate the activity measured in the case where the oral mucosa epithelial cells in the suspension of the cells were dissolved. In the case of "PBS+TritonX100," a surface active agent (Triton X-100) was added to the suspension of the cells to dissolve the cells. Besides, in the case of "PBS+Sonic," the suspension of the cells was subjected to an ultrasonic treatment to dissolve the cells.

The activities measured for the "PBS+TritonX100" and the "PBS+Sonic" were about 50 U/ml and 65 U/ml, respectively, which were higher than the activity measured in the case where the oral mucosa epithelial cells were not dissolved (see "PBS").

This suggests that in the cases of the "PBS+TritonX100" and the "PBS+Sonic," the dissolution of the cells resulted in that the activity of the alpha-amylase eluted from the oral mucosa epithelial cells, in addition to the alpha-amylase contained in the saliva mixed in, was measured. This, in turn, indicates that expression of alpha-amylase protein in the oral mucosa epithelial cells had occurred.

From the results of Example 2, it was confirmed that both expression of alpha-amylase in the oral mucosa epithelial cells at an mRNA level and expression of alpha-amylase in the cells at a protein level had taken place.

Example 3

<Examination of Circadian Rhythm of Alpha-amylase Activity>

In Example 3, diurnal variation of the activity of alpha-amylase in oral mucosa epithelial cells was searched for, and a circadian rhythm of the alpha-amylase activity was examined.

(1) A subject A (male, 32 years old) rising at 8:00 was subjected to sampling of oral mucosa epithelial cells at 1:00, 4:00, 7:00, 10:00, 13:00, 16:00, 19:00, and 22:00. Upon each sampling, the cells were suspended in 500 μL of PBS.

(2) The suspension was subjected to centrifugation (3000 rpm, 30 sec) to precipitate the cells, and the supernatant PBS was discarded. The cells thus separated were preserved in frozen state until the subsequent step.

(3) The cells were dissolved by adding thereto 100 mM of NaPO$_4$ (pH 6.0), 100 mM of NaCl, and 0.1 Triton X-100 in an amount of 30 μL. The cells thus dissolved were subjected again to centrifugation (3000 rpm, 30 sec), and the resulting supernatant was taken as a protein extract.

(4) The concentration of protein in each of the protein extracts was measured by use of BCA Protein Assay Kit (produced by PIERCE Biotechnoloty), and the concentrations of protein in the samples taken at the respective times were adjusted to 1 mg/mL.

(5) Each of the protein extracts after the protein concentration adjustment, in an amount of 25 μL, was dropped onto a chip for COCORO METER (produced by Nipro Corporation), and alpha-amylase activity was measured by use of the COCORO METER.

Incidentally, the subject A was let sleep after a sample of oral mucosa epithelial cells was taken at 1:00. At the times of measurement at 4:00 and 7:00, the subject A was once waked up for taking a sample of oral mucosa epithelial cells, and thereafter was again let sleep until the next sampling time.

Figure 8:
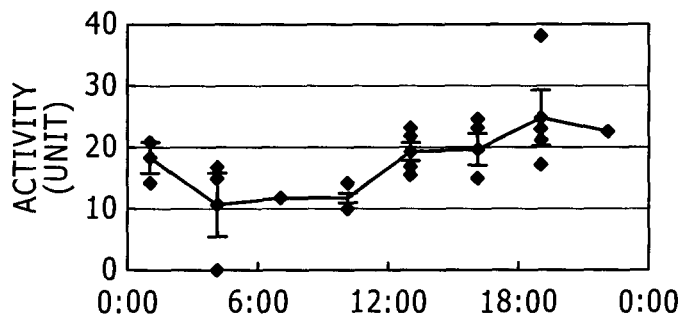
FIG. 8 is a diagram showing the measurement results (rising at 8:00) of alpha-amylase activity in Example 3.

The results are shown in FIG. 8. In the diagram, time is taken on the axis of abscissas, and the activity of alpha-amylase on the axis of ordinates.

At 9:00 of the first measurement after rising (8:00), the alpha-amylase activity was about 12 U/ml. The activity rose to about 20 U/ml at 13:00 and 16:00, and reached a maximum of about 25 U/ml at 19:00. Thereafter, the alpha-amylase activity was reduced respectively to about 22 U/ml and about 19 U/ml at 22:00 and 1:00. The alpha-amylase activities at 4:00 and 7:00 were comparable to the activity at 9:00 (about 12 U/ml).

Thus, it has been verified that the alpha-amylase activity shows a diurnal variation, which specifically represents a circadian rhythm, reaching a minimum around the rising time and a maximum at 19:00 in the evening.

Figure 9:
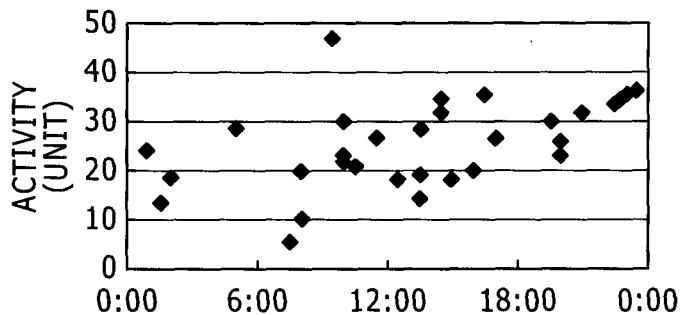
FIG. 9 is a diagram showing the activity of alpha-amylase in saliva.

For comparison, FIG. 9 shows the measurement results of the activity of alpha-amylase in saliva. In the diagram, time is taken on the axis of abscissas, and the activity of alpha-amylase on the axis of ordinates.

Unlike the alpha-amylase in the oral mucosa epithelial cells shown in FIG. 8, the activity of the alpha-amylase in the saliva does not show a circadian rhythm. It is known that the quantity of alpha-amylase secreted from salivary gland is highly sensitive to stress (see the above-mentioned Japanese Patent Laid-open Nos. 2002-168860, 2006-345869, and 2006-345870). It is considered, therefore, that variations in the quantity of alpha-amylase due to the stress at the times of measurement is one of the factors leading to the just-mentioned measurement results.

Example 4

<Examination 2 of Circadian Rhythm of Alpha-amylase Activity>

In Example 4, for the same subject A as in Example 3, a circadian rhythm of the activity of alpha-amylase in oral mucosa epithelial cells was examined, with the rising time changed from 8:00 to 6:00. Incidentally, the bedtime was after the taking of a sample of oral mucosa epithelial cells at 0.00.

(1) The subject A (male, 32 years old) rising at 6:00 was subjected to taking of a sample of oral mucosa epithelial cells at 0:00, 3:00, 6:00, 9:00, 12:00, 15:00, 18:00, and 21:00. Upon each sampling, the cells were suspended in 500 μL of PBS.

(2) The suspension was subjected to centrifugation (3000 rpm, 30 sec) to precipitate the cells, and the supernatant PBS was discarded. The same operation was again carried out. The cells thus separated were preserved in frozen state until the subsequent step.

(3) The cells were dissolved by adding thereto 20 mM of Tris-Cl (pH 7.0), 150 mM of NaCl, and lucrose Monolaurate in an amount of 30 μL. The cells thus dissolved were again subjected to centrifugation (3000 rpm, 30 sec), and the resulting supernatant was taken as a protein extract.

(4) The concentration of protein in the protein extract was measured by analysis of absorbance (280 nm).

(5) The alpha-amylase activity of the protein extract was measured by use of Salivary a-Amylase Assay Kit (produced by Salmetrics). The procedure was according to the protocol attached to the kit.

Figure 10:
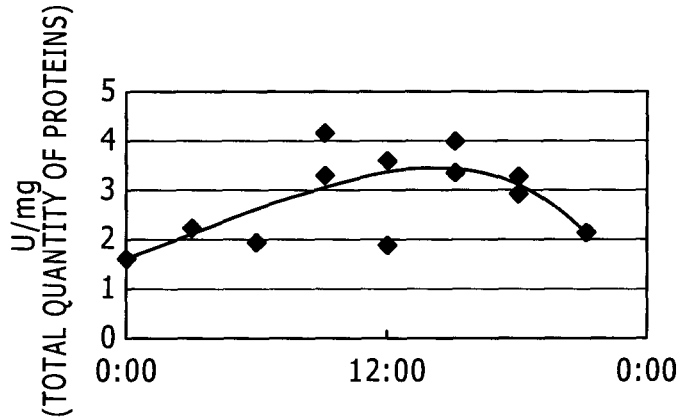
FIG. 10 is a diagram showing the measurement results (rising at 6:00) of alpha-amylase activity in Example 4.

The results are shown in FIG. 10. In the diagram, time is taken on the axis of abscissas, and the activity on the axis of ordinates. Incidentally, the activity values shown are those obtained from the activity measured in (5) above through standardization with the quantity of protein calculated in (4) above.

With the rising time changed to 6:00, the circadian rhythm of the alpha-amylase activity exhibited a maximum (about 3.5 U/mg) at 15:00. Thus, the time when the maximum was measured was four hours ahead, as compared with that in the case of rising at 8:00 (see FIG. 8). This suggests that the change of the rising time caused a deviation (lag) of the subject's biological rhythm.

From the results of Examples 3 and 4, it has been verified that the activity of alpha-amylase in oral mucosa epithelial cells shows a circadian rhythm and, further, the circadian rhythm may be varied under the influence of the rising time.

Example 5

In Example 5, four subjects were subjected to shifting of biological rhythm (sleep-wake rhythm) by 10 hours behind the original, according to the following schedule, to generate a factitious internal desynchronization (jet lag) state.

(1) The first day: Oral mucosa epithelial cells were collected at an interval of four hours, starting from 17:30. The bedtime was 23:30. The taking of a sample of the oral mucosa epithelial cells was started at 17:30, and was repeated at an interval of four hours thereafter.

(2) The second day: The rising time 7:30. After the rising, the subjects were let awake until 9:30 on the next day (the third day), thereby shifting the sleep-wake rhythm. The sampling at 1:30 and 5:30 before the rising time was conducted by momentarily waking the subjects. From then on, the sampling during the sleeping hours was similarly conducted by momentarily waking the subjects.

(3) The third day: Bedtime 9:30. The rising time 17:30.

(4) The fourth to eighth days: The sleep-wake rhythm with a bedtime of 9:30 and a rising time of 17:30 was maintained.

(5) The activity of alpha-amylase in the oral mucosa epithelial cells sampled was measured in the same manner as in Example 4.

Figure 11:
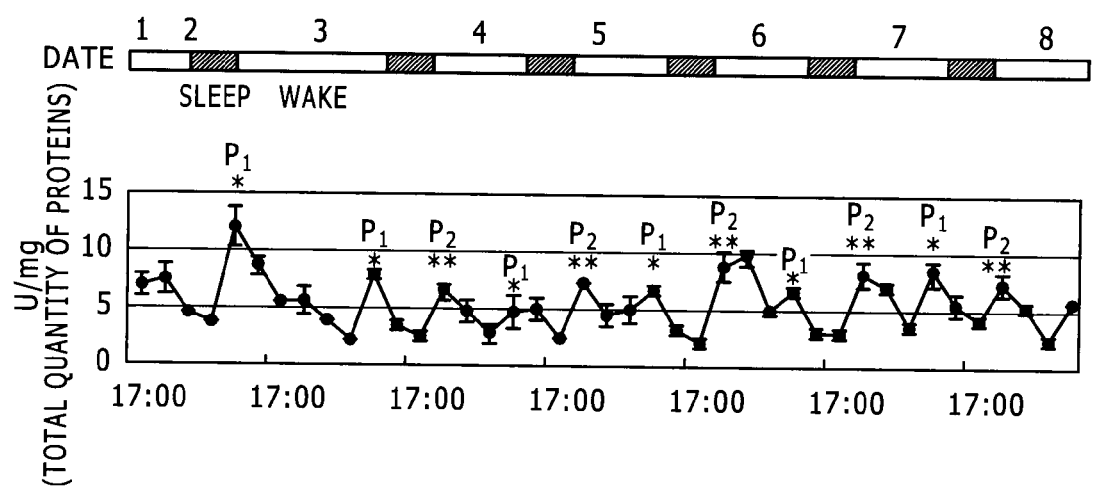
FIG. 11 is a diagram showing the measurement results (rising at 6:00) of alpha-amylase activity in Example 5.

The results are shown in FIG. 11. In the diagram, time is taken on the axis of abscissas, and the activity of alpha-amylase on the axis of ordinates.

Before the bedtime (9:30) on the second and third days when the sleep-wake rhythm had not yet been shifted, a local maximum of alpha-amylase activity was measured at 9:30 (see symbol "$p_1$" in the diagram). In this case, the circadian rhythm of the alpha-amylase activity is monophasic.

On the fourth day when the sleep-wake rhythm had already been shifted, and then on, appearance of a new local maximum of activity at 21:30 was confirmed (see symbol "$p_2$"). In this case, the circadian rhythm of the alpha-amylase activity has been changed to be diphasic.

These results show that, by detecting the polyphasic rhythm exhibited in the circadian rhythm of the alpha-amylase activity, the internal desynchronization (jet lag) generated in the subject due to a shift of the sleep-wake rhythm can be detected.

Figure 12:
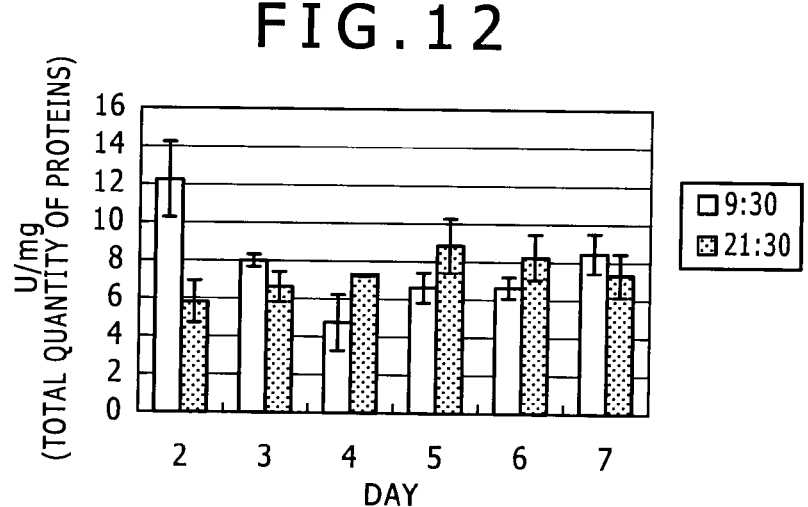
FIG. 12 is a diagram showing the activities of alpha-amylase at times of 9:00 and 21:00 on the second to seventh days.

FIG. 12 is a diagram showing the alpha-amylase activity on the second to seventh days, at 9:30 and 21:30 which are the times when the diphasic local maxima were observed after the shift of the sleep-wake rhythm.

On the second day when the sleep-wake rhythm had not yet been shifted, the alpha-amylase activity at 9:30 was sufficiently greater than the activity at 21:30.

On the other hand, on the fourth day when the sleep-wake rhythm had already been shifted, and then on, the alpha-amylase activity at 9:30 was gradually lowered, and, on the contrary, the activity at 21:30 was raised gradually. This shows that the subject was gradually recovering from the internal desynchronization generated in the subject due to the shift of the sleep-wake rhythm, and that the subject's biological rhythm was being gradually synchronized with the sleep-wake rhythm after the shifting, namely, the sleep-wake rhythm with a bedtime of 9:30 and a rising time of 17:30.

Accordingly, it has been verified by the above results that, based on the magnitude or amplitude ratio of the diphasic local maxima of the activity observed at 9:30 and 21:30, it is possible to determine the degree of the internal desynchronization, or the deviation (lag) of biological rhythm, in the subject or the condition of the recovery from the deviation (lag).

Industrial Applicability

According to the method pertaining to the present invention, an activity variation curve showing the variation with time of the activity of alpha-amylase is utilized as a molecular timetable, whereby a biological rhythm intrinsic of each subject can be estimated in a simple and minimally invasive manner. Therefore, it becomes possible for each individual to know a biological rhythm peculiar to himself or herself, to set optimum medication time, acting time and eating time, which, in turn, is useful for realization of chronotherapy, for exhibition of personal ability, and for a diet.

Furthermore, when a deviation (lag) of biological rhythm is detected by the method according to the present invention, the detection results can be used for prevention of various diseases which might arise from a deviation of biological rhythm, and for improvement of poor physical conditions such as jet lag.

The Sequence Listing text file named 12667180seqlisting.txt, which has a creation date of Jan. 17, 2013, and a size of 754 bytes, is incorporated by reference herein in its entirety.

The invention claimed is:

1. A method of acquiring information about variation with time of alpha-amylase activity, comprising:
 providing a plurality of samples of oral mucosa epithelial cells from the organism, said oral mucosa epithelial cells being separated from saliva, and said samples having been taken at different times; and
 chemically assaying alpha-amylase enzymatic activity in the plurality of samples, thereby detecting variation with time of alpha-amylase activity.

2. The method according to claim 1, wherein an activity variation curve showing the variation of the activity with time is utilized as a molecular timetable for estimating a biological rhythm of the organism.

3. The method according to claim 2, wherein a deviation of the biological rhythm is detected based on the number of local maxima of the activity which the activity variation curve shows in one day by use of the molecular timetable.

4. The method according to claim 2, wherein a deviation of the biological rhythm of the organism is detected by collating the molecular timetables formed a plurality of times for the organism.

5. The method according to claim 2, wherein a deviation of the biological rhythm of the organism is detected by collating, with the molecular timetable, the activity of the biologically active agent at a predetermined time.

6. The method according to claim 2, wherein a deviation of the biological rhythm is detected based on the number of local minima of the activity which the activity variation curve shows in one day by use of the molecular timetable.

7. The method of claim 1, wherein the chemically assaying step comprises chemically assaying alpha-amylase enzymatic activity in a plurality of protein extracts prepared from the plurality of samples of oral mucosa epithelial cells.

8. The method of claim 7, wherein the plurality of protein extracts were prepared by a process comprising exposing the oral mucosa epithelial cells to a solution comprising an agent for dissolving the cells.

9. The method of claim 8, wherein the agent for dissolving the cells comprises a surface-active agent.

10. The method of claim 7, wherein the plurality of protein extracts were prepared by a process comprising physically disrupting the oral mucosa epithelial cells.

11. The method of claim 10, wherein the oral mucosa epithelial cells were physically disrupted by a process comprising ultrasonic treatment.

12. The method of claim 1, wherein the plurality of samples of oral mucosa epithelial cells were taken from the organism were taken at different times in one day.

* * * * *